United States Patent [19]

Gross et al.

[11] 4,059,684

[45] Nov. 22, 1977

[54] BONE CEMENT COMPOSITIONS CONTAINING GENTAMYCIN

[75] Inventors: Albert Gross, Frankfurt am Main; Roland Schaefer, Friedrichsdorf, Taunus; Siegfried Reiss, Bad Homburg, all of Germany

[73] Assignee: Kulzer & Co. GmbH, Bad Homburg, Germany

[21] Appl. No.: 656,668

[22] Filed: Feb. 9, 1976

[30] Foreign Application Priority Data

Mar. 14, 1975  Germany .......................... 2511122

[51] Int. Cl.$^2$ ............................................. A61K 31/78
[52] U.S. Cl. ........................................ 424/4; 424/14; 424/81; 536/17
[58] Field of Search ................. 536/17; 424/181, 180, 424/4

[56] References Cited

U.S. PATENT DOCUMENTS

3,915,955  10/1975  Cooper et al. ..................... 536/17

FOREIGN PATENT DOCUMENTS

2,022,117  11/1971  Germany .......................... 536/17

*Primary Examiner*—Johnnie R. Brown
*Attorney, Agent, or Firm*—Burgess, Dinklage & Sprung

[57] ABSTRACT

A bone cement composition includes, as the principal component, powdered copolymers of methyl methacrylate and methyl acrylate, or monomeric methyl methacrylate, and, in addition, gentamicin hydrochloride and/or gentamicin hydrobromide, or a mixture of gentamicin sulfate with sodium chloride, potassium chloride, sodium bromide and/or potassium bromide. The bone cement composition is used, for example, for cementing implants in place, for the anchoring of endoprostheses of the joints, in the treatment of skull defects, and for carrying out spinal fusions. The composition provides for antibiotic release in higher concentrations to prevent infections.

13 Claims, No Drawings

BONE CEMENT COMPOSITIONS CONTAINING GENTAMYCIN

BACKGROUND

The invention relates to a foreproduct for the preparation of bone cement, which contains, in addition to a gentamicin compound, either copolymers of methylmethacrylate and methylacrylate in powder form or monomeric methylmethacrylate, as its principal component.

Bone cements are used, for example, for cementing implants in place, for the anchoring of endoprostheses of the joints, in the treatment of skull defects, and for the performance of spinal fusion. They are obtained by mixing together foreproducts composed of homopolymers or copolymers of methylmethacrylate in powder form and of suitable liquid monomers, usually methylmethacrylate, a catalyst system and, in some cases, X-ray contrast agents such as zirconium dioxide or barium sulfate, for example, dyes for the identification of the cement in the body, and other additives, to prepare a plastic dough, which is then placed in the body and set "in situ" by polymerization of the monomer. The catalyst system is a so-called "redox" system composed of an organic peroxy compound, usually dibenzoyl peroxide, as the catalyst, plus a reducing component (accelerator) such as dimethyl-p-toluidine. Thus, for example, the bone cement known from German "Auslegeschrift" No. 2,229,702 is prepared from polymethylmethacrylate and a monomer mixture of methylmethacrylate and methacrylic acid esters of higher alcohols, and a catalyst system consisting of dibenzoyl peroxide and dimethyl-p-toluidine.

For prophylaxis against infections at the boundary surface between the bone cement and the bone, such as can occur when the natural hip joint is replaced with an artificial one and the socket and the femoral shank are anchored by means of bone cement, antibiotics are added to the bone cement. Such a bone cement or glue is known from German "Offenlegungsschrift" No. 2,022,117, in which penicillin, gentamicin and tetracycline are given as examples of suitable antibiotics. One product which is commercially available for the preparation of bone cement contains gentamicin sulfate.

The antibiotic is at first released from the hardened bone cement in a relatively high concentration to assure its bactericidal and bacteriostatic action. Then, however, a diminution of the concentration takes place; the release rate, which is now lower, remains relatively constant over a longer period of time, and can properly be termed a sustained release; however, the active concentration of the antibiotic is low. In this manner, infections can be largely prevented by the released antibiotic during the early post-operative hours, but due to the reduction of the concentration later infections cannot be reliably prevented or combatted.

The possibility of increasing the effective concentration by the addition of greater amounts of antibiotic is limited, because such addition would impair the mechanical strength of the hardened bone cement.

THE INVENTION

This invention provides a composition for the preparation of bone cement, from which the antiobiotic will be released in a higher concentration.

This is achieved in the composition described above by the fact that it contains, in accordance with the invention, gentamicin hydrochloride and/or gentamicin hydrobromide, or a mixture of gentamicin sulfate with sodium chloride, potassium chloride, sodium bromide and/or potassium bromide. Gentamicin hydrochloride is especially suitable. If a mixture of gentamicin sulfate and the abovenamed alkali metal halides is to be used, sodium chloride and/or potassium bromide are preferred.

The foreproduct of the invention can contain the gentamicin hydrohalide or the mixture of gentamicin sulfate and alkali metal halide, as the case may be, together with copolymers of methylmethacrylate and methyl acrylate in powder form, a suitable catalyst—especially an organic peroxy compound, preferably dibenzoyl peroxide, and X-ray contrast agents and other conventional additives, such as dyes, for example. X-ray contrast agents, especially zirconium dioxide or barium sulfate, are added in the amount of about 5 to 15 weight-percent with respect to the polymer-containing foreproduct. The copolymers are prepared from mixtures of methyl methacrylate with methyl acrylate in which the content of the latter amounts to approximately 3 to 30 weight-percent.

The foreproduct can also be in the form of a suspension prepared from the gentamicin hydrohalide or from the mixture of gentamicin sulfate and the alkali metal halides, monomeric methylmethacrylate, and a suitable reducing component, preferably dimethyl-p-toluidine.

The polymer-containing foreproduct contains from 1.25 to 5 weight-percent and the monomer-containing foreproduct contains from 2.5 to 10 weight-percent of gentamicin, in the form of the hydrochloride, hydrobromide or sulfate. The proportion of alkali metal halide, when mixtures of gentamicin sulfate and the abovenamed alkali metal halides are used, amounts to from 0.5 to 10 weight-percent, and preferably to from 1 to 5 weight-percent in the polymer-containing foreproduct, and from 1 to 20 weight-percent, preferably 2 to 10 weight-percent, in the monomer-containing foreproduct.

The preparation of the bone cement is accomplished by mixing the foreproduct, containing the antibiotic, polymer and peroxide, with the antibiotic-free monomer containing the reducing component, or by mixing the foreproduct containing the antibiotic, the monomer and the reducing component with the antibiotic-free polymer containing the peroxide. It is also possible, however, to mix together the foreproduct containing the antibiotic, polymer and peroxide and the foreproduct containing the antibiotic, monomer and reducing component. The plastic dough thus obtained is put into the patient's body and there it is hardened "in situ". During the sustained-release phase, the gentamicin hydrohalide is released at a rate that is three to five times higher than the release rate of gentamicin sulfate, i.e., the concentration of the active substance at the boundary surface between the bone cement and the bone is three times to five times higher.

By the use of the foreproduct of the invention, an augmented release of the antibiotic is thus achieved without increasing the amount of the antibiotic, while at the same time the good mechanical properties of the hardened bone cement remain unimpaired, and consequently a reliable bactericidal or bacteriostatic action is brought about over a longer period than in the case of known bone cements. Even when mixtures of gentamicin sulfate and the abovenamed alkali halides are used, a three-fold to five-fold increase is achieved in the rate of release of the antibiotic in the sustained-release phase in comparison to gentamicin sulfate only.

EXAMPLES

In the following examples the composition of foreproducts pursuant to the invention will be described. The antibiotic that is added is identified by its biologically determined activity coefficient (AC), which indicates the number of milligrams of antibiotically active base (gentamicin) per gram of the salt.

EXAMPLE 1

Foreproduct containing polymer and gentamicin hydrochloride:
 4.75 g of a powdered mixture of copolymers of methyl methacrylate with methyl acrylate
 25 mg of dibenzoyl peroxide
 89 mg of gentamicin hydrochloride, AC 703 (corresponds to 62.5 mg of gentamicin).

This foreproduct is mixed with 2.5 ml of methyl methacrylate containing 2 wt.-% of dimethyl-p-toluidine and 60 ppm of hydroquinone as stabilizer. The dough thus prepared is placed in the patient's body and hardened "in situ".

If it is required, 0.5 g of zirconium dioxide or barium sulfate is added to the foreproduct described in this example, to serve as an X-ray contrast agent.

EXAMPLE 2

Foreproduct containing monomer and gentamicin hydrochloride:
 2.5 ml of methyl methacrylate, containing
 2 wt.-% of dimethyl-p-toluidine and
 60 ppm of hydroquinone,
 89 mg of gentamicin hydrochloride, AC 703 (corresponds to 62.5 mg of gentamicin)

This foreproduct is mixed with 5 g of a powdered mixture of copolymers of methyl methacrylate with methyl acrylate and 0.5 wt.-% of dibenzoyl peroxide. The dough thus prepared is placed in the body and hardened in situ.

EXAMPLE 3

Foreproduct containing polymer, gentamicin sulfate and sodium chloride:
 4.75 g of a powdered mixture of copolymers of methyl methacrylate with methyl acrylate,
 25 mg of dibenzoyl peroxide
 250 mg of finely divided sodium chloride
 103 mg of gentamicin sulfate, AC 605 (corresponds to 62.5 mg of gentamicin).

This foreproduct is mixed with 2.5 ml of methyl methacrylate containing 2 wt.-% of dimethyl-p-toluidine and 60 ppm of hydroquinone. The dough obtained is placed in the patient's body and hardened in situ.

If an X-ray contrast agent is required, 0.7 g of zirconium dioxide or barium sulfate is added to the foreproduct described in this example.

Instead of the sodium chloride, 250 mg of a finely divided mixture composed of 95 wt.-% sodium chloride, 2 wt.-% potassium chloride, 2wt.-% calcium chloride and 1 wt.-% sodium bicarbonate can be used.

EXAMPLE 4

Foregoing containing polymer, gentamicin sulfate and potassium bromide:
 4.75 g of a powdered mixture of copolymers of methyl methacrylate and methyl acrylate,
 25 mg of dibenzoyl peroxide,
 250 mg of finely divided potassium bromide,
 103 mg of gentamicin sulfate, AC 605 (corresponds to 62.5 mg of gentamicin).

This foreproduct is mixed with 2.5 ml of methyl methacrylate containing 2 wt.-% of dimethyl-p-toluidine and 60 ppm of hydroquinone. The dough thus prepared is placed in the body and hardened in situ.

If an X-ray contrast agent is required, 0.5 g of zirconium dioxide or barium sulfate, for example, is added to the foreproduct described in this example.

EXAMPLE 5

Foreproduct containing monomer, gentamicin sulfate and sodium chloride:
 2.5 ml of methyl methacrylate,
 2 wt.-% of dimethyl-p-toluidine,
 60 ppm of hydroquinone
 103 mg of gentamicin sulfate, AC 605 (corresponds to 62.5 mg of gentamicin),
 100 mg of finely divided sodium chloride.

This foreproduct is mixed with 5 g of a powdered mixture of copolymers of methyl methacrylate with methyl acrylate and 0.5 wt.-% of dibenzoyl peroxide. The dough thus prepared is placed in the body and hardened in situ.

EXAMPLE 6

Foreproduct containing monomer, gentamicin sulfate and potassium bromide:
 2.5 ml of methyl methacrylate,
 2 wt.-% of dimethyl-p-toluidine
 60 ppm of hydroquinone
 103 mg of gentamicin sulfate, AC 605 (corresponds to 62.5 mg of gentamicin),
 100 mg of finely divided potassium bromide.

This foreproduct is mixed with 5g of a powdered mixture of copolymers of methyl methacrylate with methyl acrylate and 0.5 wt.-% of dibenzoyl peroxide. The dough thus prepared is placed in the body and hardened in situ.

The doughs prepared with the foreproducts of Examples 1 to 6 are adequate for use in finger joint operations, for example. In hip joint operations multiples of these amounts are used, usually about 40 g of polymer and 20 ml of monomer. The amounts of the other components specified in the examples are increased by the same factor.

In order to determine and compare the release of the antibiotic from materials obtained by the use of the foreproducts of the invention, test specimens were prepared containing:
 1. Gentamicin sulfate
 2. Gentamicin hydrochloride
 3-a. Gentamicin sulfate and 2 wt.-% NaCl
 3-b. Gentamicin sulfate and 5 wt.-% Nacl
 4-a. Gentamicin sulfate and 2 wt.-% KBr and
 4-b. Gentamicin sulfate and 5 wt.-% KBr.

For this purpose intimate mixtures were prepared from:

1.

5 g of a powder prepared from a mixture of copolymers of methyl methacrylate and methyl acrylate, 0.5 wt.-% of dibenzoyl peroxide and 103 mg of gentamicin sulfate (corresponding to 62.5 mg of gentamicin) and 2.5 ml of methyl methacrylate containing 2 wt.-% of dimethyl-p-toluidine and 60 ppm of hydroquinone;

2.

5 g of a powder prepared from a mixture of copolymers of methyl methacrylate and methyl acrylate, 0.5 wt.-% of dibenzoyl peroxide and 89 mg of gentamicin hydrochloride (corresponding to 62.5 mg of gentamicin) and 2.5 ml of methyl methacrylate containing 2 wt.-% of dimethyl-p-toluidine and 60 ppm of hydroquinone;

3-a.

5.26 g of a powder prepared from a mixture of copolymers of methyl methacrylate and methyl acrylate, 0.5 wt.-% of dibenzoyl peroxide, 103 mg of gentamicin sulfate (corresponding to 62.5 mg of gentamicin) and 105 mg of finely divided sodium chloride and 2.5 ml of methyl methacrylate containing 2 wt.-% of dimethyl-p-toluidine and 60 ppm of hydroquinone;

3-b.

5.41 g of a powder prepared from a mixture of copolymers of methyl methacrylate and methyl acrylate, 0.5 wt.-% of dibenzoyl peroxide, 103 mg of gentamicin sulfate (corresponding to 62.5 mg of gentamicin) and 270 mg of finely divided sodium chloride and 2.5 ml of methyl methacrylate containing 2 wt.-% of dimethyl-p-toluidine and 60 ppm of hydroquinone;

4-a.

5.26 g of powder prepared from a mixture of copolymers of methyl methacrylate and methyl acrylate, 0.5 wt.-% of dibenzoyl peroxide, 103 mg of gentamicin sulfate (corresponding to 62.5 mg of gentamicin) and 103 mg of finely divided potassium bromide and 2.5 ml of methyl methacrylate containing 2 wt.-% of dimethyl-p-toluidine and 60 ppm of hydroquinone;

4-b.

5.41 g of a powder prepared from a mixture of copolymers of methyl methacrylate and methyl acrylate, 0.5 wt.-% of dibenzoyl peroxide, 103 mg of gentamicin sulfate (corresponding to 62.5 mg of gantamicin) and 270 mg of finely divided potassium bromide and 2.5 ml of methyl methacrylate containing 2 wt.-% of dimethyl-p-toluidine and 60 ppm of hydroquinone.

The antibiotic contained in the mixtures 1, 3a, 3b, 4a and 4b has the activity coefficient 605 (AC 605); the one contained in Mixture 2 has an activity coefficient of 703 (AC 703).

The mixtures becoming plastic and dough-like after one minute were pressed in a three-part metal mold under a pressure of 3 atmospheres, to form pore-free test specimens 5 cm long, 0.6 cm thick and 1 cm wide, weight 3.78 grams. The polymerization was complete in 7 minutes.

The test bodies obtained were immersed in 10 ml of distilled water in test tubes which were placed in a drying oven at 37° C. After 1, 2, 4, 7, 14, 21, 28, 35, 42 and 49 days, the water was removed and replaced with fresh water. The antibiotic released from the test specimens was determined spectrophotometrically at 570 nm by means of the ninhydrin method. To prepare the test solution, a solution of 1 g of ninhydrin and 50 ml of ethylene glycol monomethyl ether, and a solution of 40 mg of tin(II) chloride in 50 ml of citrate buffer (pH 4.5), were mixed together in a 1:1 ratio before beginning the measurement. The evaluation was performed using a calibration curve obtained with gentamicin sulfate. The test amounts obtained by pouring from the test specimens were placed each in a 25 ml measuring flask; 5 ml of reagent solution was added, and the mixture was kept for 15 minutes in a boiling water bath. After the specimens had cooled, each was increased to a volume of 25 ml with 50% ethanol.

The amounts of antibiotic detected in the test solutions are given in Table I, in terms of milligrams of biologically active base (gentamicin).

A comparison of the values in Columns 2 (hydrochloride), 3a (sulfate + 2 wt.-% NaCl), 3b (sulfate + 5 wt.-% NaCl), 4a (sulfate + 2 wt.-% KBr) and 4b (sulfate + 5 wt.-% KBr) with those in Column 1 (sulfate only) clearly reveals the increase in the rate of release of the antibiotic from the test specimens containing the hydrochloride or containing the sulfate mixed with sodium chloride or potassium bromide, as compared with the use of gentamicin sulfate alone.

The foreproduct of the invention is suitable also for the preparation of articles for implantation into human or animal bodies. For this purpose, a doughy mixture is prepared, in some cases from the foreproduct containing polymer and catalyst with the addition of monomer and reducing component, and in other cases from the foreproduct containing the monomer and the reducing component with the addition of polymer and catalyst, and the mixture is allowed to set in a mold under pressure, for example, to form the desired objects. The objects can be of any desired shape, but is desirable that they be spherical.

TABLE I

| Time (day) | 1 Sulfate | 2 Hydrochloride | 3 Sulfate (a) +2% NaCl | 3 Sulfate (b) +5% NaCl | 4 Sulfate (a) +2% KBr | 4 Sulfate (b) +5% KBr |
|---|---|---|---|---|---|---|
| 1 | 1.16 | 1.54 | 1.23 | 1.26 | 1.325 | 1.325 |
| 2 | 0.067 | 0.169 | 0.135 | 0.202 | 0.078 | 0.093 |
| 4 | 0.029 | 0.169 | 0.117 | 0.292 | 0.026 | 0.105 |
| 7 | 0.032 | 0.267 | 0.162 | 0.324 | 0.298 | 0.198 |
| 14 | 0.000 | 0.323 | 0.238 | 0.476 | 0.380 | 0.518 |
| 21 | 0.080 | 0.326 | 0.266 | 0.427 | 0.268 | 0.380 |
| 28 | 0.052 | 0.181 | 0.288 | 0.393 | 0.348 | 0.412 |
| 35 | 0.041 | 0.308 | 0.263 | 0.337 | 0.345 | 0.414 |
| 42 | 0.069 | 0.162 | 0.276 | 0.414 | 0.380 | 0.494 |
| 49 | 0.039 | 0.254 | 0.370 | 0.575 | 0.590 | 0.818 |

The values in columns 1 to 4 indicate the amount of released biologically active base (gentamicin) in milligrams.

What is claimed is:
1. A bone cement comprising the composition A or B, wherein:
A comprises as the principal component a powdered copolymer of methyl methacrylate and methyl acrylate and 1.25 to 5 weight percent gentamycin in the form of the hydrochloride hydrobromide or 1.25 to 5 weight percent gentamycin in the form of the sulfate in admixture with 0.5 to 10 weight percent of sodium chloride, potassium chloride, sodium bromide or potassium bromide, and B comprises as the principal component monomeric methyl methacrylate and 2.5 to 10 weight percent gentamycin in the form of the hydrochloride hydrobromide or 2.5 to 10 weight percent of gentamycin in the form of the sulfate together with 1 to 20 weight percent of sodium chloride, potassium chloride, sodium bromide or potassium bromide.

2. A bone cement according to claim 1 comprising a powdered copolymer of methyl methacrylate and methyl acrylate.

3. Composition of claim 1 containing gentamicin hydrochloride.

4. Composition of claim 1 containing a mixture of gentamicin sulfate and sodium chloride.

5. Composition of claim 1 containing a mixture of gentamicin sulfate and potassium bromide.

6. Composition of claim 1 wherein a catalyst, especially dibenzoyl peroxide, is contained in the powdered copolymers of methyl methacrylate and methyl acrylate.

7. Composition of claim 1 wherein a reducing component, especially dimethyl-p-toluidine, is contained in the monomeric methyl methacrylate.

8. Composition of claim 1 wherein an x-ray contrast agent is added to the powdered copolymerizates of methyl methacrylate and methyl acrylate.

9. Composition of claim 1 comprising monomeric methacrylate and 2.5 to 10 weight percent of gentamycin in the form of the hydrochloride or hydrobromide.

10. A composition according to claim 1 comprising a powdered copolymer of methyl methacrylate and methyl acrylate and 1.25 to 5 weight percent gentamycin in the form of the sulfate in admixture with 0.5 to 10 weight percent of a salt mixture of 95 weight percent sodium chloride, 2 weight percent potassium chloride, 2 weight percent calcium chloride and 1 weight percent sodium bicarbonate.

11. Use of the composition of claim 1 for the preparation of hardened, implantable articles.

12. Use of the composition of claim 1 for the preparation of hardened, implantable, spherical articles.

13. Composition of claim 1 comprising monomeric methyl methacrylate and 2.5 to 10 weight percent of gentamycin in the form of the sulfate together with 1 to 20 weight percent of sodium chloride, potassium chloride, sodium bromide or potassium bromide.

* * * * *

UNITED STATES PATENT AND TRADEMARK OFFICE
CERTIFICATE OF CORRECTION

PATENT NO. : 4059684
DATED : November 22, 1977
INVENTOR(S) : ALBERT GROSS et al

It is certified that error appears in the above-identified patent and that said Letters Patent are hereby corrected as shown below:

Column 6, penultimate line, after "hydrochloride" insert -- or --.

Column 7, line 6, after "hydrochloride" insert -- or --.

Signed and Sealed this

Thirteenth Day of June 1978

[SEAL]

Attest:

RUTH C. MASON
Attesting Officer

DONALD W. BANNER
Commissioner of Patents and Trademarks